Nov. 26, 1963
C. FISCHER
GLADIOLUS PLANT
Filed July 5, 1962
Plant Pat. 2,317
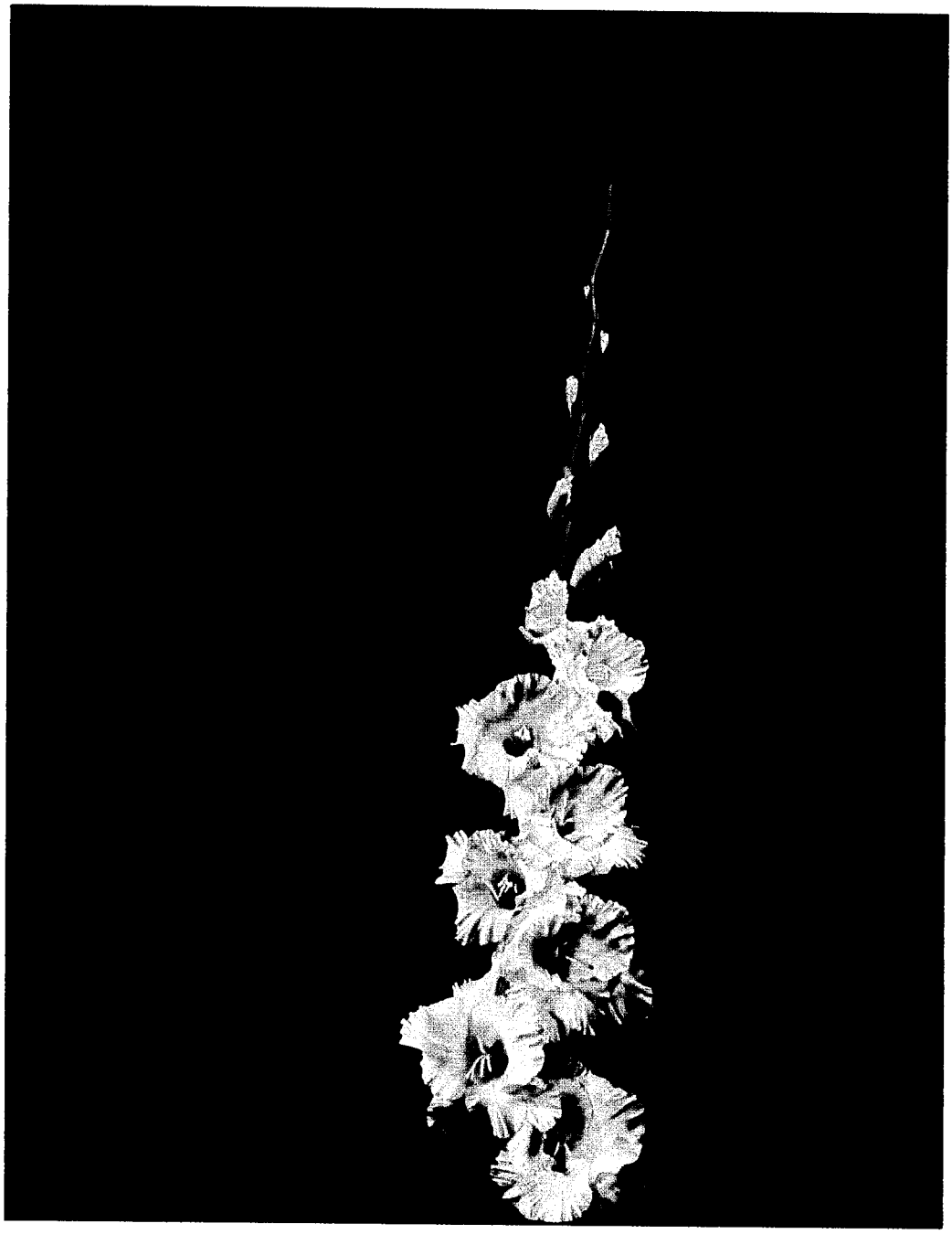
Inventor
Carl Fischer
By: Robb & Robb
Attorneys.

United States Patent Office

Plant Pat. 2,317
Patented Nov. 26, 1963

2,317
GLADIOLUS PLANT

Carl Fischer, St. Charles, Minn., assignor to Imperial Flowers Limited, Leamington, Ontario, Canada, a corporation of Canada Filed July 5, 1962, Ser. No. 207,831
1 Claim. (Cl. Plt.—85)

The present invention relates to a new and distinct variety of gladiolus plant which was originated by me by crossing the variety "Southern Belle" (unpatented) with an unnamed and unpatented seedling derived from a cross of "Greta Garbo" (unpatented) × "Elizabeth the Queen" (unpatented), the variety "Southern Belle" being the seed parent and the unnamed seedling being the pollen parent.

The foregoing cross was made by me by manual cross pollination as performed in my outdoor breeding fields at St. Charles, Minnesota, and had for its objective the production of a new gladiolus variety which bears superior white flowers of supreme beauty. This objective was fully achieved, along with other commercially desirable features, as evidenced by the following unique combination of characteristics which are outstanding in the new variety and which distinguish it from its parents, as well as from all other varieties of which I am aware:

(1) An extremely ruffled form of the flower petals;

(2) A precise flower form, giving the flowers a carved or chiseled appearance; and (3) Distinctive and attractive buds which have a Mimosa Yellow general color tonality in the opening stage, but which develop into attractive open flowers of supreme beauty, said open flowers being Ivory White in their general color tonality, with a somewhat more intensely colored throat.

My new variety resembles the variety known as "June Wedding" (unpatented) more than any other, but differs principally therefrom by having a taller habit of growth; a later blooming habit; a heavier petal substance; more heavily ruffled flower petals; a deeper cream colored flower throat; and good color retention of the flowers without any tendency to revert to pink color as is characteristic of the flowers of "June Wedding."

Asexual reproduction of my new variety by cormels through several generations, as performed by me at St. Charles, Minnesota, shows that the foregoing characteristics and distinctions come true to form and are established and transmitted through succeeding propagations.

The accompanying drawing shows a typical specimen flower spike of my new variety, with the flowers in different stages of development ranging from closed buds through partially open buds to fully open flowers, as depicted in color as nearly true as it is reasonably possible to make the same in a color illustration of this character.

The following is a detailed description of my new variety, with color terminology in accordance with the Horticultural Colour Charts issued by the British Colour Council and the Royal Horticultural Society, except where general color terms of ordinary dictionary significance are obvious:

Locality where grown and observed: St. Charles, Minnesota.

Propagation: Holds its distinguishing characteristics through succeeding propagations by plantings derived from cormels.

*Plant*

Growth: Extremely rugged; excellent propagator; blossom spike ranges from about 60 inches to 64 inches tall.

Blooming habit: Mid-season bloomer in the Northern latitudes of the United States; comes into bloom from large bulbs in about 85 days.

Stems: Straight; willowy.

*Diameter at base.*—½ inch.

*Color (just above the bulb).*—White.

Foliage: Fan-shaped, with upright leaves; leaves average 1½ inches wide; leaves attain height averaging about 42 inches; healthy. Color—blue-green.

Disease resistance: Unusually good resistance to Fusarium yellows, Sclerotina dry rot and Septoria leaf spot, as determined by comparison with other varieties grown in my fields near St. Charles, Minnesota, in irrigated black loam soil.

Corms (bulbs): Round; smooth; covered well by thick and heavy husks. Color of flesh—between Amber Yellow, Plate 505/1 and Amber Yellow, Plate 505/2.

*Flower*

Spike: Tall; bears 19 or 20 buds, with 7 or 8 florets opening at one time, and with from 5 to 7 buds showing color.

Bud:

*Size.*—About 3 inches long when opening.

*Opening.*—From 5 to 7 buds show color at one time; buds open well.

Flower:

*Arrangement.*—Florets are semi-formally arranged on stem and usually all face forward.

*Size.*—Lower individual florets average from 5 inches to 5½ inches in diameter, with upper florets being progressively smaller.

*Form.*—Florets are round, recurved, needle-pointed and ruffled, giving appearance of pure white lace.

*Keeping qualities.*—Keeps well.

Petals:

*Shape.*—Round; extremely ruffled; recurved.

*Size.*—Outer petals—about 2¾ inches wide. Lip petal—about 1¾ inches wide.

*Aspect.*—Extremely heavy substance; smooth surface.

*Fragrance.*—None.

*Color.*—Basic color is Ivory White, with slightly more intensely colored throat; opening buds are tinted Mimosa Yellow, Plate 602/3, but become white as soon as florets open.

*Reproductive Organs*

Stamens: Color—pure white.

Pistil: Color—pure white.

I claim:

A new and distinct variety of gladiolus plant, substantially as herein shown and described, characterized particularly as to novelty by the unique combination of an extremely ruffled form of the flower petals, a relatively precise flower form which gives the effect of a chiseled or carved appearance, and distinctive and attractive buds which are tinted Mimosa Yellow in the opening stage, but which develop into exceptionally attractive open flowers of Ivory Yellow general color tonality, said open flowers having a somewhat more intensely colored throat.

No references cited.